(12) United States Patent
Manz et al.

(10) Patent No.: US 7,060,979 B2
(45) Date of Patent: Jun. 13, 2006

(54) TRANSMISSION SENSOR

(75) Inventors: Rolf Manz, Oehringen (DE); Gerhard Steiner, Pfedelbach-Unterhöfen (DE); Reinhard Wierling, Pfedelbach-Unterhöfen (DE); Johann Schenkl, Neunburg (DE); Martin Brabec, Nabburg (DE)

(73) Assignees: Mahle Filtersysteme GmbH, Stuttgart (DE); emz-Hanauer GmbH & Co. KgaA, Nabburg (DE)

( * ) Notice: Subject to any disclaimer, the term of this patent is extended or adjusted under 35 U.S.C. 154(b) by 300 days.

(21) Appl. No.: 10/475,406

(22) PCT Filed: Apr. 22, 2002

(86) PCT No.: PCT/DE02/01465

§ 371 (c)(1),
(2), (4) Date: Oct. 22, 2003

(87) PCT Pub. No.: WO02/086463

PCT Pub. Date: Oct. 31, 2002

(65) Prior Publication Data

US 2004/0135089 A1    Jul. 15, 2004

(30) Foreign Application Priority Data

Apr. 23, 2001   (DE) ............................... 101 19 932

(51) Int. Cl.
*G01N 21/05* (2006.01)

(52) U.S. Cl. ...................................... 250/343; 356/440

(58) Field of Classification Search ................ 250/343; 356/440
See application file for complete search history.

(56) References Cited

U.S. PATENT DOCUMENTS

| | | | |
|---|---|---|---|
| 3,809,912 A | 5/1974 | Henning | |
| 4,017,193 A | 4/1977 | Loiterman | |
| 4,257,708 A | 3/1981 | Fukuda | |
| 4,775,794 A * | 10/1988 | Behmann | 250/373 |
| 5,350,922 A * | 9/1994 | Bartz | 250/338.5 |
| 5,589,935 A | 12/1996 | Biard | |
| 5,828,458 A * | 10/1998 | Taylor et al. | 356/440 |
| 5,875,783 A | 3/1999 | Kullik | |
| 6,264,836 B1 * | 7/2001 | Lantis | 210/188 |
| 6,464,798 B1 | 10/2002 | Rosenbauer et al. | |
| 6,746,610 B1 | 6/2004 | Manz et al. | |

FOREIGN PATENT DOCUMENTS

| | | |
|---|---|---|
| DE | 197 14 664 | 10/1998 |
| DE | 198 06 559 | 8/1999 |
| DE | 199 57 592 | 6/2001 |
| WO | WO/01/40701 | 11/2000 |

* cited by examiner

*Primary Examiner*—Otilia Gabor
(74) *Attorney, Agent, or Firm*—Collard & Roe, P.C.

(57) ABSTRACT

The invention relates to a transmission sensor (1) for measuring the turbidity of a fluid, comprising a first and a second measuring section (2, 3). A transmitter (6) emits electromagnetic radiation into the two measuring sections (2, 3). A first receiver (14) is allocated to the first measuring section (2) and a second receiver (15) is allocated to the second measuring section (3). The transmitter (6) is inserted into a transmitter carrier (8) in such a way that the transmitter (6) is forced to adopt a predetermined oriented position. The receivers (14, 15) are inserted into a receiver carrier (18) in such a way that each of said receivers (14, 15) is forced to adopt a predetermined oriented position. A transmitter carrier holder (9) forcibly positions the transmitter carrier (8) in a predetermined location and a receiver carrier holder (19) forcibly positions the receiver carrier (18) in a predetermined location.

21 Claims, 5 Drawing Sheets

TRANSMISSION SENSOR

CROSS REFERENCE TO RELATED APPLICATIONS

Applicants claim priority under 35 U.S.C. §119 of German Application No. 101 19 932.5 filed on Apr. 23, 2001. Applicants also claim priority under 35 U.S.C. §365 of PCT/DE02/01465 filed on Apr. 22, 2002. The international application under PCT article 21(2) was not published in English.

BACKGROUND OF THE INVENTION

1. Field of the Invention

This invention relates to a transmission sensor suitable for measuring turbidity of a fluid. This invention also relates to the use of such a transmission sensor and a method of operation using it.

2. The Prior Art

German Patent Application DE 199 57 592.4 of Nov. 30, 1999 discloses a transmission sensor having a lengthy first measurement zone and a shorter second measurement zone. The two measurement zones are filled with a fluid, the turbidity of which is to be measured during operation of the sensor. The known transmission sensor has a housing with a wall that is transparent for electromagnetic radiation, in particular light, at least in the area of the measurement zones. The transmission sensor has a transmitter, which is arranged in the housing and emits electromagnetic radiation, in particular infrared light, into the measurement zones through an inlet area in the wall. A first receiver of the transmission sensor is situated in the housing and senses the radiation passing through the first measurement zone through a first outlet area in the wall. In a corresponding manner, a second receiver, which is also situated in the housing, senses the radiation transmitted through the second measurement zone through a second outlet area in the wall. The known transmission sensor thus has two independent signal pathways or radiation pathways within the fluid, in particular light pathways, which differ with regard to the path traveled by the radiation between the transmitter and the receiver. By comparing the received signals sensed at the receivers, it is possible to determine the degree of contamination of the fluid, i.e., the turbidity of the fluid.

With the help of such a transmission sensor, a turbidity can be measured in a fluid in particular, where this turbidity develops when the fluid is mixed, i.e., contaminated with solid foreign matter (suspension) and/or liquid foreign matter (emulsion).

Transmission sensors of this type are used, for example, in oil systems that work with hydraulic oils or lubricant oils. For environmental protection reasons, hydraulic oils and lubricant oils should be designed to be environmentally friendly, in particular biodegradable. These requirements result in oils having a comparatively low stability with respect to hydrolytic cleavage when they come in contact with water. In the case of oils, in particular oils that are capable of rapid biological degradation, however, even with traditional mineral oils, a low water content therefore contributes greatly to a long oil lifetime. An unacceptably high water content may lead to aging products, in particular by hydrolysis, and may cause problems with materials and functions in equipment that is supplied with and/or working with such oil. Since water content in oil causes turbidity, in particular in the infrared range, it is possible to monitor the water content in oil by means of such a transmission sensor in order to be able to shut down the respective oil system promptly on reaching a critical water content, for example.

In such an oil system, a so-called "coalescer" may be provided for elimination of water; a coalescer removes water from oil passing through it. Since such a coalescer functions like a fine filter, permanent flow through the coalescer rapidly leads to clogging due to other noncritical impurities entrained by the oil. To prevent such premature clogging of the coalescer, the water content in the oil must be measured with the greatest possible accuracy, so the oil stream passes through the coalescer only when needed.

A transmission sensor of the type defined in the preamble may also be used in a plurality of other applications. For example, with the help of such a transmission sensor, it is possible to monitor the degree of contamination of rinse water in a dishwashing machine or a washing machine, so that fresh water can be added as a function of this degree of contamination. This makes it possible to reduce fresh water consumption. Furthermore, in the food industry, in particular in the beverage industry, such a transmission sensor may be used to monitor the quality of the liquid achieved in production. Likewise, the quality of drinking water and/or wastewater can be monitored by such a transmission sensor. In addition to measuring the turbidity in liquids, the transmission sensor is also suitable for measuring turbidity in gases, e.g., for detection of smoke and/or steam. In particular, such a transmission sensor may be used in a clean room or in an ultraclean room for monitoring the dust content in the air.

SUMMARY OF THE INVENTION

The present invention is concerned with the problem of providing possibilities for ensuring economical production of the transmission sensor in the case of a transmission sensor of the type defined in the preamble.

This problem is solved according to this invention by a transmission sensor having the features of Claim 1.

This invention is based on the general idea of using sensors and receivers in a respective carrier, where the respective carrier is designed so that a predetermined aligned position is necessarily obtained for the sensor and/or for the receiver. In addition, a holder is provided for this carrier, the holder being designed so that a predetermined position necessarily results for the particular carrier in the housing. Due to these features, very inexpensive standard components, i.e., diodes or transistors may be used for the transmitter and the receiver. Due to the use of the carriers and the holders, this ensures that these inexpensive components will be positioned more or less automatically within relatively narrow position tolerances in the desired manner in the sensor when the sensor is assembled, without requiring any particular manual skill. Therefore, production does not require any increased care and can easily be automated. These measures thus lead to a transmission sensor which can be manufactured relatively easily and inexpensively by mass production.

Inexpensive transmitters in particular have a relatively great scattering with respect to the direction of emission of the radiation emitted. Various measures are proposed for reducing the influence of these scattering effects on the radiation intensity arriving at the receivers.

Transmitter aperture arrangements may be connected downstream from the transmitter to thereby blank out interfering outside ranges of the radiation. Alternatively or additionally, a receiver aperture arrangement may be connected upstream from each receiver to thereby reduce the passage of light scatter to the particular receiver. Such an aperture arrangement may be formed by one aperture or by a flush alignment of a pair of apertures, i.e., by two apertures arranged in alignment with one another, or by a tunnel, a so-called collimator. In addition, it has been found that with relatively short measurement zones, scattering effects, in particular a so-called small-angle scattering, have a particularly strong effect. To prevent this, for a further embodiment it is proposed that any distance between the transmitter and receiver be designed to be at least approximately ten times longer than the outlet diameter of the transmitter aperture arrangement allocated to it.

According to an especially advantageous embodiment, the sensor may be designed to emit various electromagnetic rays which differ in wavelength. This measure makes it possible to detect a change in color within the fluid, preferably within a liquid, with the help of the transmission sensor. For example, it is possible in this way to detect contamination of a first liquid with a second liquid which is soluble in it, in particular a liquid of a different color. To this end, a sensor may have a plurality of transmitter elements which generate radiation of different wavelengths. It is also possible to design a signal transmitter element so that it can emit rays of different wavelengths. For example, there are known two-color LEDs or duo LEDs which can be switched between two wavelengths with regard to their light emission.

The transmission sensor according to this invention is suitable in a special manner for use in detection of solid and/or liquid impurities in a liquid and for detection of solid and/or liquid impurities in a gas.

The problem on which the present invention is based is also solved by an operating method having the features of Claim 11. In the inventive operating method, a measured value calibration is performed, in which a first calibration value, which correlates with the intensity of the radiation transmitted through the first measurement zone, and a second calibration value, which correlates with the intensity of the radiation transmitted through the second measurement zone, are determined. In determination of a turbidity value which correlates with the turbidity of the fluid, standardized measured values are used. A first measured value, which correlates with the intensity of the radiation transmitted through the first measurement zone, and a second measured value, which correlates with the intensity of the radiation transmitted through the second measurement zone, are determined first. Then a first standardized measured value is formed by the quotient of the first measured value and the first calibration value, and a second standardized measured value is formed from the quotient of the second measured value and the second calibration value. The turbidity value is then determined on the basis of these standardized measured values.

With the help of this procedure, the condition of the fluid prevailing at the time of calibration of the measured value is defined as the reference condition, so that the turbidity value thus determined indicates the deviation from this reference condition. This makes it possible to eliminate the effects of dirt deposits on the transmitter and/or on the receivers, i.e., on the particular wall sections of the sensor through which the radiation passes. Likewise, phenomena associated with aging of the transmitter and/or receiver are neutralized. In addition, this neutralizes fluctuations in the output power of the transmitters and receivers used, which may occur in particular in the production of inexpensive electronic components within manufacturing tolerances. The method proposed according to this invention thus supports the use of inexpensive components.

To determine the turbidity value from the standardized measured values, it is possible to determine, for example, a difference between the standardized measured values. This difference may then be used to form a turbidity factor, which may be used for additional investigations, tests, controls and regulations. An especially expedient embodiment is one in which a turbidity factor formed by the quotient of the second standardized measured value and the first standardized measured value is used to determine the turbidity value which correlates with the turbidity of the fluid.

The problem on which this invention is based is also solved by an operating method having the features of Claim 14. In this operating method, a transmitter calibration is performed, in which the transmitter output power of the transmitter is increased incrementally until a predetermined minimum value for the incoming radiation intensity can be detected at both receivers. The transmitter output power which then prevails is used as the operating transmitter output power with which the transmitter is operated in determination of a turbidity value which correlates with the turbidity of the fluid. The predetermined minimum values mentioned above ensure that an increase in turbidity can still be detected with certainty on the basis of the starting condition at which the transmitter calibration is performed. The incremental increase in transmitter output power ensures that an operating power for the subsequent measurement operation will be discovered, this operating power being just high enough so that an increase in turbidity can be reliably ascertained based on the starting condition which prevails at the time of calibration of the transmitter. Through these measures, it is usually possible to operate the transmitter at a significantly lower transmitter output power than the maximum allowed transmitter output power of the transmitter. In this way, the lifetime of the transmitter can be increased significantly. The operating method according to this invention therefore allows the use of inexpensive transmitters, which essentially have a short lifetime anyway, but it can be increased to an adequate extent by this invention.

It is clear that the two operating methods according to this invention for which patent protection is claimed independently of one another may also be implemented cumulatively.

Other important features and advantages of the present invention are derived from the subclaims, the drawings and the respective description of the figures on the basis of the drawings.

It is self-evident that the features mentioned above, which are to be described in greater detail below, may be used not only in the particular combination given but also alone or in any other combinations without going beyond the scope of the present invention.

BRIEF DESCRIPTION OF THE DRAWINGS

Preferred exemplary embodiments of this invention are illustrated in the drawings and are explained in greater detail in the following description.

The Drawings show schematically.

BRIEF DESCRIPTION OF PREFERRED EMBODIMENTS

Figure 1:
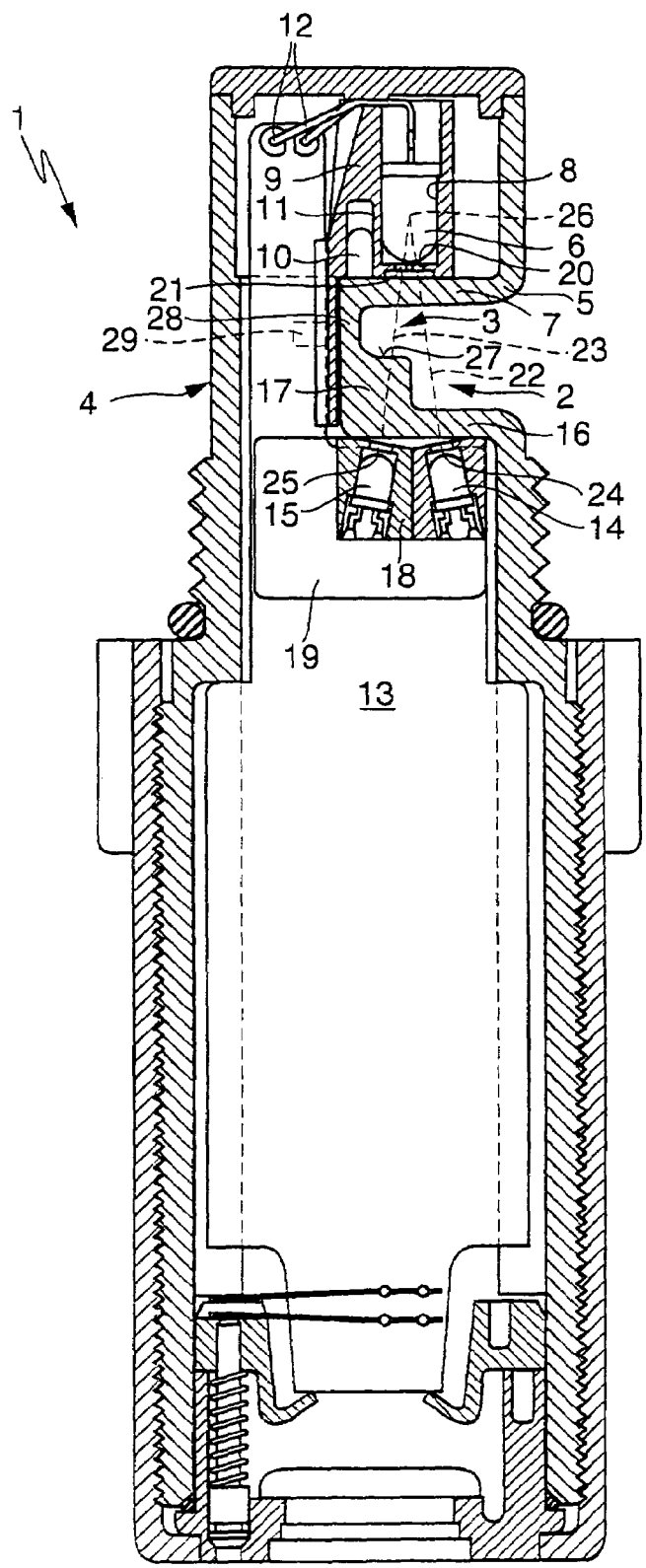
FIG. 1 a longitudinal section through a transmission sensor according to this invention.

According to FIG. 1 an inventive transmission sensor 1 has a longer first measurement zone 2 and a shorter second measurement zone 3. During operation of the transmission sensor 1, the two measurement zones 2 and 3 are filled by a fluid (not shown here), e.g., a liquid or a gas which is to be monitored for impurities. The transmission sensor 1 has a housing 4, which has at least one wall 5 that is transparent for electromagnetic radiation, at least in the area of the measurement zones 2 and 3. This housing 4 is preferably manufactured as an injection molded part made of plastic.

A transmitter 6, e.g., in the form of a semiconductor element, is provided in the housing 4 close to an inlet area 7 in the wall 5. This transmitter 6 is capable of emitting electromagnetic radiation through the inlet area 7 into the measurement zones 2 and 3. The preferred electromagnetic radiation here is light, in particular infrared light. The transmitter 6 is mounted in a transmitter carrier 8, which is designed so that the transmitter necessarily assumes a predetermined aligned position on insertion into the transmitter carrier 8. The transmitter carrier 8 is in turn designed on a transmitter carrier holder 9, which necessarily positions the transmitter carrier 8 in the housing 4 in a predetermined position in the inlet area 7 by means of suitable positioning means. These positioning means may consist, for example, of an alignment pin 10 and a fitting opening 11, which cooperates with it. The transmitter 6 is connected at 12 to a circuitboard 13, which carries a circuit for operation of the transmission sensor 1.

In its housing 4, the transmission sensor 1 also has a first receiver 14 and a second receiver 15, which may also be formed by semiconductor elements. While the first receiver 14 is assigned to the first measurement zone 2 and a first outlet area 16 of the wall 5, the second receiver 15 is assigned to the second measurement zone 3 and a second outlet area 17 of the wall 5. For the two receivers 14 and 15, a common receiver carrier 18 is provided, the receivers 14 and 15 being inserted into corresponding receptacles in this carrier. The receiver carrier 18 is designed so that the receivers 14, 15, which are inserted into it, necessarily both assume a predetermined aligned position. A receiver carrier holder 19 is provided for the receiver carrier 18, necessarily positioning the receiver carrier 18 in the housing 4 in such a way as to result in a predetermined positioning on the outlet areas 16 and 17 for the receivers 14 and 15. This receiver carrier holder 19 is necessarily mounted on the circuitboard 13.

The injection mold which is used to manufacture the housing 4 may be equipped with a high-grade planar surface having minimal roughness in the section which shapes the inlet area 7 and the outlet areas 16 and 17, so that the housing 4, which is formed by injection molding, has the same high-quality surface in these sections of the wall 5.

The transmitter carrier 8 has a first transmitter aperture arrangement 20 and a second transmitter aperture arrangement 21 between the transmitter 6 and the inlet area 7. The first transmitter aperture arrangement 20 is assigned to the first measurement zone 2 and is arranged in a first beam path 22 represented by a broken line. Accordingly, the second transmitter aperture arrangement 21 is assigned to the second measurement zone and is arranged in a second beam path 23, represented by a broken line. Similarly, a first receiver aperture arrangement 24 is also provided on the receiver carrier 18 between the first receiver 14 and the first outlet area 16, and a second receiver aperture arrangement 25 is arranged between the second receiver 15 and the second outlet area 17. The first receiver aperture arrangement 24 is arranged in the first beam path 22 and the second receiver aperture arrangement 25 is arranged in the second beam path 23 accordingly. Each of the aperture arrangements 20, 21, 24 and 25 is formed here by an aperture and/or a tunnel. If it is assumed that the particular aperture opening is of a negligible extent in the direction of the beam, then this is an aperture. However, if it is of an extent with a constant opening cross section in the direction of the beam, it is a tunnel. Any desired intermediate states are also possible here. As an alternative, the aperture arrangements may each also be formed by a pair of apertures comprising two apertures positioned in mutual alignment in the direction of the beam, preferably having the same opening cross section.

To reduce the influence of scattering effects, it has been found to be expedient to have the distances between the transmitters 6 and the receivers 14, 15 be at least ten times longer than the outlet diameter or opening diameter of the particular assigned transmitter aperture arrangement 20 and/or 21. If both transmitter aperture arrangements 20 and 21 have the same outlet diameter, then the shorter second measurement zone 3 should be at least ten times longer than this outlet diameter.

To achieve reproducible, reliable and accurate measurement results, it has proven to be advantageous to coordinate the lengths of the two measurement zones 2 and 3 in such a way that the ratio of the shorter second measurement zone 3 to the longer first measurement zone 2 has a maximum value of 5:7. A ratio of 5:10 has proven to be optimum.

If the two receivers 14 and 15 are assigned a common transmitter 6 as in the exemplary embodiment depicted according to FIG. 1, then the two beam paths 22 and 23 intersect at point 26 in the transmitter 6. The first beam path here extends from the transmitter 6 to the first receiver 14, while the second beam path 23 extends from the transmitter 6 to the second receiver 15.

In the embodiment according to FIG. 1, the different measurement zones 2 and 3 are formed by the fact that the wall 5 has a step 27 in the area of the measurement zones 2 and 3. The wall thickness in the second outlet area 17 is accordingly greater than in the first outlet area 16. Due to this design, the arrangement of the two receivers 14 and 15 is simplified. In another embodiment, the wall thicknesses of the two outlet areas 16 and 17 may be selected to be equal in size, in which case an offset arrangement of the receivers 14 and 15 is then possible.

In a lateral area 28 of the wall 5, a third receiver 29 may be accommodated in the housing 4; the receiver is indicated with broken lines here and is arranged at the side of the measurement zones 2 and 3. While the first two receivers 14 and 15 sense the radiation transmitted the measurement zones 2 and 3, the third receiver 29 is able to detect the radiation scattered in the fluid. This may be advantageous for particular measurement purposes and applications of the transmission sensor 1.

For conventional applications of the transmission sensor 1, one transmitter 6 which emits electromagnetic rays at a certain wavelength is sufficient, but for other applications in which a change in color in a liquid is to be detected, it may be expedient to design the transmitter 6 so that it can emit different electromagnetic radiation which differs in its wavelength. The transmission measurements are then performed at different wavelengths and compared. A change in color in the fluid may have different effects on the transmission at different wavelengths. Due to the transmitter 6, which can be switched between at least two wavelengths, this effect can be used to determine a change in color.

Figure 2:
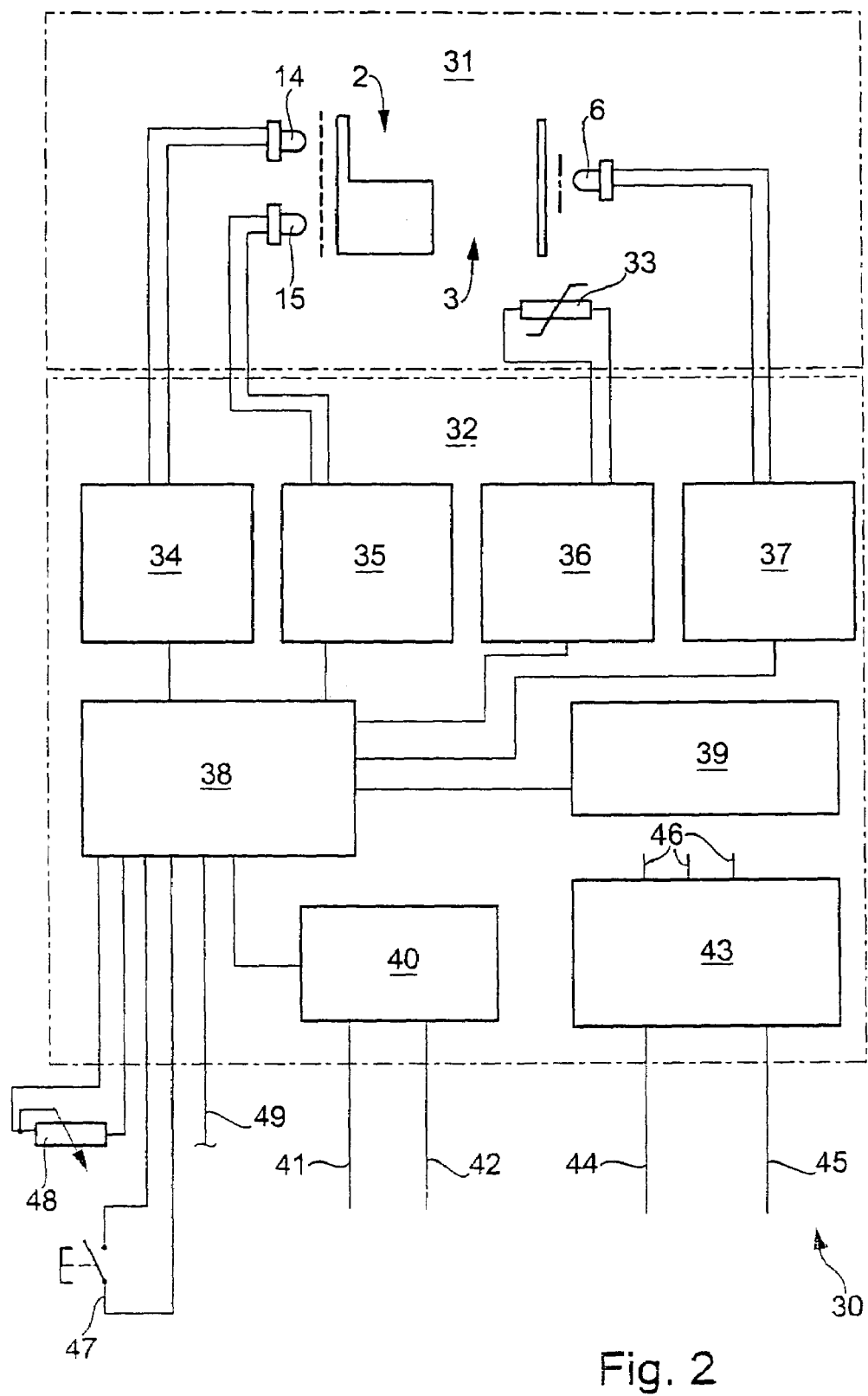
FIG. 2 a block diagram of a circuit configuration for the transmission sensor according to FIG. 1.

According to FIG. 2, a circuit 30 for a transmission sensor 1 according to FIG. 1 is divided functionally and optionally also physically into an optical region 31, shown at the top of FIG. 2, and an analysis region 32, shown at the bottom of FIG. 2. At least the optical region 31 having the measurement zones 2 and 3, the transmitter 6 and the receivers 14 and 15 is accommodated in the housing 4 of the transmission sensor 1. In addition, a temperature sensor 33 may also be provided, e.g., in the form of an NTC (negative temperature coefficient) resistor, which is used to measure the temperature in the fluid and accordingly is also situated expediently on the transmission sensor 1 in or on an area exposed to the fluid.

The analysis region 32, which may essentially also be situated in the housing 4 of the transmission sensor 1, e.g., on the circuitboard 13, has an amplifier 34 for the first receiver 14, an amplifier 35 for the second receiver 15 and an amplifier 36 for the temperature sensor 33. A current transformer 37 for transforming the current of the transmitter 6 is provided for the transmitter 6. The amplifiers 34, 35, 36 and the current transformer 37 are connected to a microprocessor 38. This microprocessor 38 is also connected to a rewritable permanent memory 39, e.g., an EEPROM. In addition, the microprocessor 38 is connected to an output driver 40, which signals a turbidity value that has been determined and/or signals the operating readiness of the arrangement over output lines 41 and 42. The circuit 30 is connected via a voltage stabilizer 43 and connecting lines 44 and 45 to a power supply. The individual current consumers of the circuit 30 are connected to this voltage stabilizer 43 by terminals 46.

The microprocessor 38 is also connected to a switch 47 with which the calibration processes according to this invention, as explained in greater detail below, can be initialized. In addition, an adjustment device 48 is provided, e.g., a potentiometer, which is connected to the microprocessor 38 and is used, for example, for setting a limit value or alarm value for the turbidity of the liquid to be tested. Finally, an interface 49 may be provided so that the microprocessor 38 and/or the circuit 30 can be connected by this interface to an external analyzer device, e.g., a personal computer. In this way, it is possible to plot and analyze the curve of turbidity over time, for example.

Figure 3:
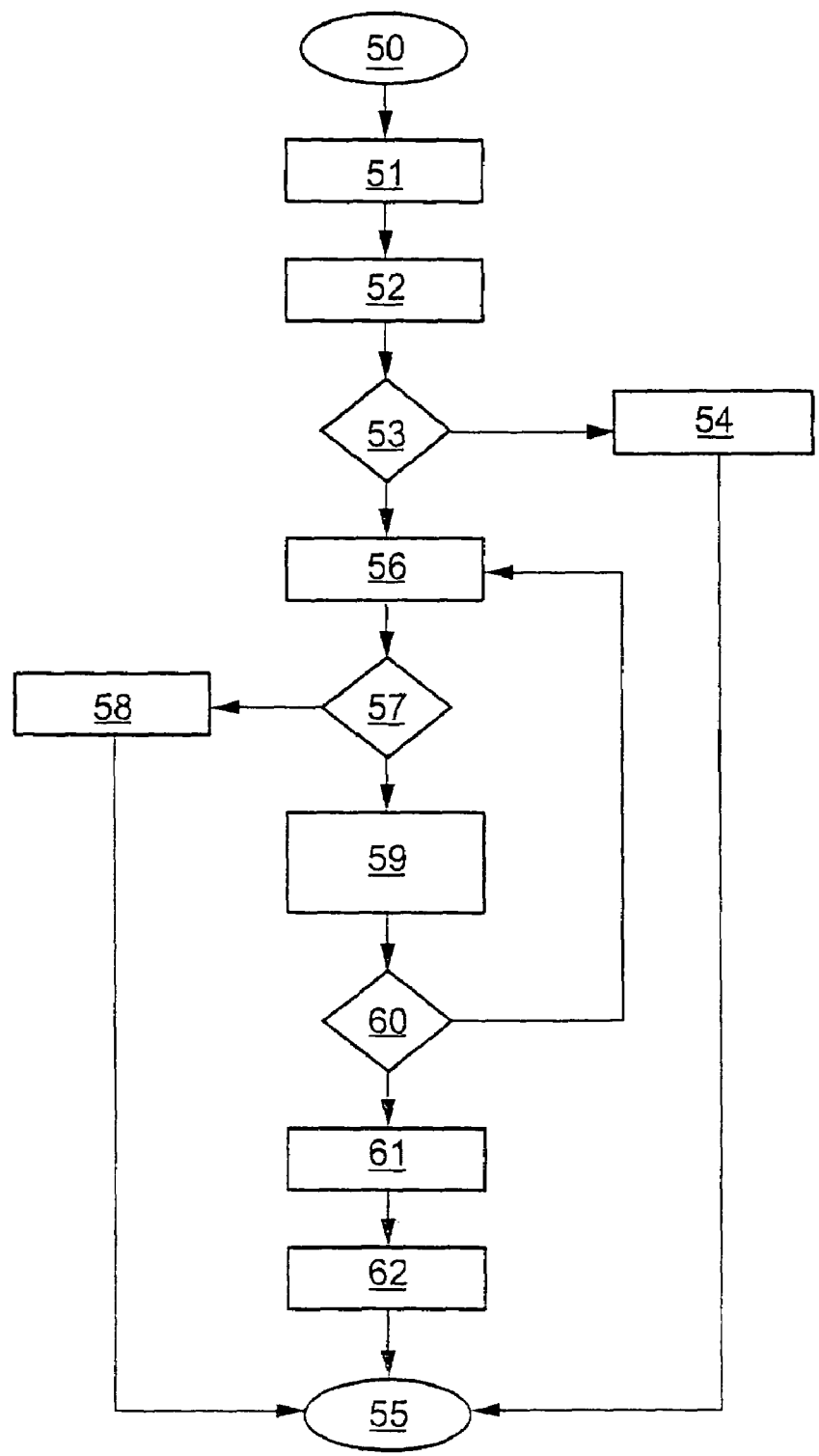
FIG. 3 a flow chart for a measured value calibration and for a transmitter calibration according to this invention.

FIG. 3 shows a simplified flow chart for implementation of a calibration process according to this invention. This diagram shows a starting point 50 for the calibration process. For example, a calibration process is started when the switch 47 according to FIG. 1 is operated manually. Likewise it is possible for the microprocessor 38 to trigger the start 50 of the calibration process.

In the present invention a distinction is made between a measured value calibration and a transmitter calibration. However, it is quite possible for these two calibration operations to be performed in a joint combined calibration operation. This joint combined calibration operation is depicted in FIG. 3.

After the start 50, first a value for a calibrated operating transmitter output power of the transmitter 6 is set at zero. Since the transmitter output power correlates with the current supplied, the transmitter output power is indicated below as I; accordingly, the calibrated operating transmitter output power is $I_{cal}$. In step 51, $I_{cal}$ is therefore set at 0 mA. In a subsequent step 52, in the preferred embodiment depicted here, the prevailing temperature of the fluid is determined with the help of the temperature sensor 33. A query 53 determines whether the temperature thus detected is a predetermined minimum temperature which may be, for example, 0° C. when testing the water content in oil. If the outcome of this query 53 is negative, i.e., if the prevailing temperature has not reached the required minimum temperature, an error message is generated at 54 and the calibration operation is terminated at 55. The microprocessor 38 may send the error message as a signal to the user over the interface 49 and over the output driver 40.

If the query 53 has a positive outcome, then in step 56 the calibrated operating transmitter output power $I_{cal}$ is incremented by a certain amount. For example, the current supplied is increased by 0.2 mA. Then there is a query 57, which ascertains whether the instantaneous operating transmitter output power and/or the respective current $I_{ca}$ is below a predetermined upper limit value, which may be 50 mA, for example. If the outcome of this query is negative, then the operating transmitter output power, i.e., the respective current is too high, so a corresponding error message is generated at 58 and the calibration operation is terminated at 55. However, if the outcome of the query 57 is positive, the instantaneous operating current and/or the operating transmitter output power is below the upper limit value, so the process continues with step 59. In this step 59, the transmitter 6 is activated and operated at the instantaneous operating transmitter output power $I_{cal}$, i.e., the current set at that instant is supplied. In the case of this transmitter power $I_{cal}$ at both receivers 14 and 15, the radiation intensity which is detectable there, i.e., the incoming radiation intensity, is measured at both receivers. The first measured value $M1_{cal}$ detectable at the first receiver 14 is determined and corresponds to a voltage that can be picked up for example at the first receiver 14. The situation is similar for a second measured value $M2_{cal}$. After measuring the radiation intensities arriving at receivers 14 and 15, the current for the transmitter 6 is turned off again. This procedure ensures that the transmitter 6 will always receive current and be operated with current when and only when a measurement is being performed. In this way, the lifetime of the transmitter 6 as well as that of the receivers 14 and 15 is increased. To further reduce the activity of the transmitter 6 in order to increase component lifetime, the current transformer 27 may operate the transmitter 6 by PWM (pulse width modulation).

After determination of the measured values $M1_{cal}$ and $M2_{cal}$, a query 60 ascertains whether a predetermined minimum value for the incoming radiation intensity can be detected at both receivers 14 and 15. For example, a signal of 4 volts should be detectable at each of the two receivers 14 and 15. If the required minimum radiation intensity is detectable at only one of the two receivers 14 and 15 or if the predetermined minimum cannot be detected at both receivers 14 and 15, then the process loops back from the query 60 to the incrementation in step 56 to raise the operating transmitter output power $I_{cal}$ by one additional increment. For example, the current supplied is increased by 0.2 mA more. This results in an incremental increase in the transmitter output power of the transmitter 6 until query 60 obtains the result that the predetermined minimum for the incoming radiation intensity has been reached at both receivers 14 and 15. Thus, if query 60 has a positive outcome, a signal or a message can be enabled in step 61 to show that an initial state for the fluid has been detected such that increasing turbidity due to impurities will be detectable in subsequent measurements. In step 62 the instantaneous value of the transmitter output power $I_{cal}$ as well as the measured values $M1_{cal}$ and $M2_{cal}$ measured thereby are stored in memory 39. Then the calibration operation is terminated at 55. The transmitter output power determined in this way is used as the operating transmitter output power $I_{cal}$ for subsequent turbidity measurements. Likewise, the measured values so determined are used as calibration values $M1_{cal}$ and $M2_{cal}$ which are used in this invention for standardizing the measured values of subsequent turbidity measurements.

The transmitter calibration according to this invention is the procedure for determining the operating transmitter output power $I_{cal}$. The inventive measured value calibration consists of determining measured values and defining them as calibration values $M1_{cal}$ and $M2_{cal}$ with an initial state which prevails during the calibration operation.

With the help of switch 47, for example, the presence of a sufficiently clear fluid can then be defined manually, for example, if after adding new oil to an oil system, it is assumed that the oil is sufficiently clear. To this extent the actuation of the switch 47 constitutes a higher-level signal with which the calibration operations described above can be initiated.

Figure 4:
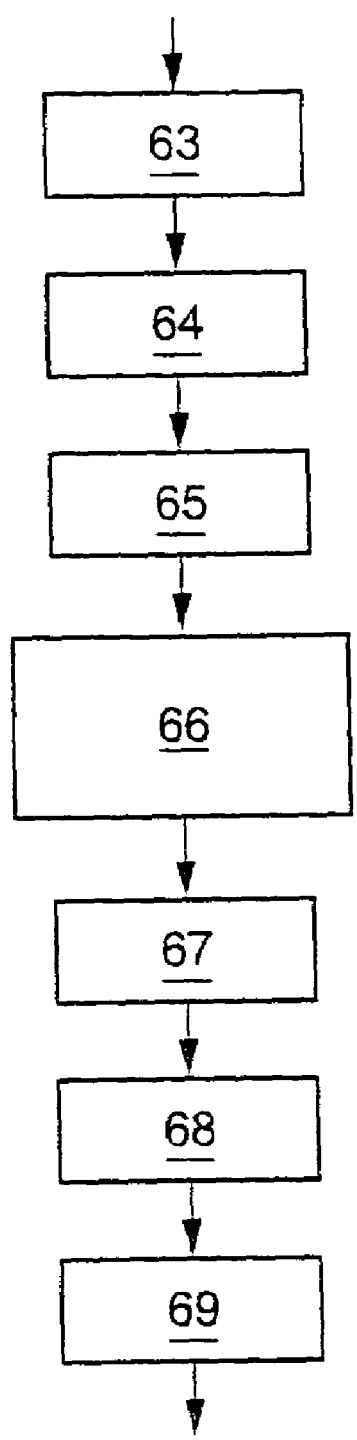
FIG. 4 a flow chart for the inventive determination of a turbidity factor.

FIG. 4 shows a flow chart for a signal measurement cycle in measurement operation of the transmission sensor 1 according to FIG. 1. The transmitter 6 is activated at 63, with the transmitter 6 being operated precisely at the operating transmitter output power $I_{cal}$ determined by the calibration. In step 64, the radiation intensity arriving at receivers 14 and 15 at that instant is determined in each case, a first measured value M1 and a second measured value M2 being generated, each correlating with the corresponding radiation intensity. As soon as these measured values M1 and M2 are available, the transmitter 6 is turned off again at 65 to thereby increase the lifetime of transmitter 6 and receivers 14 and 15. In step 66, a standardization of the measured values M1 and M2 determined in step 64 is performed as proposed according to this invention with the help of the calibration values obtained by calibration. In doing so, a first stabilized measured value $M1_{standard}$ is formed by the quotients $M1/M1_{cal}$, i.e., the first measured value divided by the first calibration value. In a similar manner, a second standardized measured value $M2_{standard}$ is generated by the quotient $M2/M2_{cal}$ (second measured value divided by the second calibration value).

In a subsequent step 67, a turbidity factor f is determined; this is achieved, for example, by forming the quotient $M2_{standard}/M1_{standard}$. The turbidity factor f may also be formed as follows, for example: $(M2_{standard}-M1_{standard})/(M2_{standard}+M1_{standard})$. This turbidity factor f correlates with a turbidity value which in turn correlates with the turbidity of the fluid. In a subsequent step 68, this turbidity factor f can be weighted. For example, a check determines whether the turbidity factor f is above or below a predetermined limit value. This limit value may be set and/or varied by the adjustment device 48, for example. In addition, the instantaneous turbidity factor f may be linked to a time signal at 69 to be able to record the curve of the turbidity factor f over time. During measurement operation, this sequence 63 through 69 is repeated periodically.

For the case when the turbidity factor f thus determined has reached a predetermined threshold value, then at step 68 or step 69, a corresponding message signal may be generated. Likewise, it is possible for this message signal to be generated only when the turbidity factor f thus determined has reached the predetermined threshold value at a predetermined number (e.g., 6) of successive turbidity measurements. Errors due to short-term turbidity fluctuations can be eliminated in this way.

In a further embodiment, this message signal may activate display means, which are provided in particular on the transmission sensor 1, to the user, e.g., visually that the predetermined threshold value has been exceeded. This message, i.e., display should expediently be deactivated and/or reset only by the user, e.g., manually.

The curve of the turbidity of the fluid over time may be analyzed for example to differentiate a gradual increase in turbidity from a rapid increase in turbidity, which is indicative of a disturbance incident. Likewise, it is possible to predict when the particular fluid system will have to be shut down for maintenance purposes.

Figure 5:
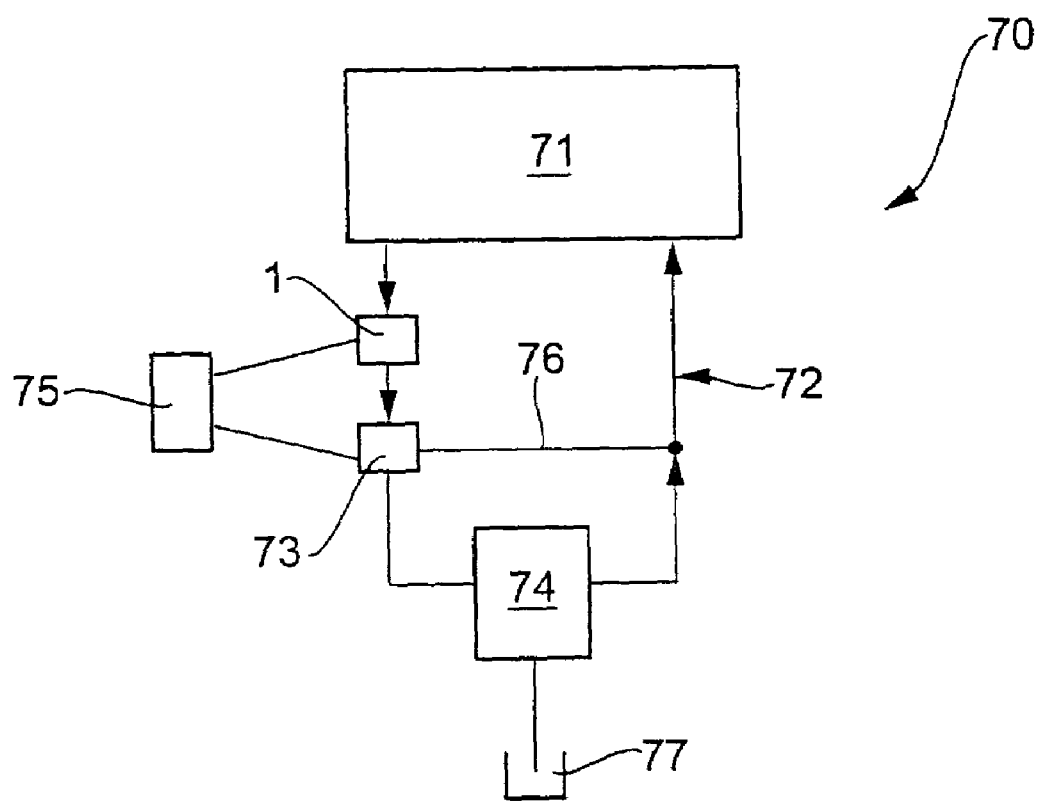
FIG. 5 a block diagram for use of a transmission sensor according to this invention as shown in FIG. 1.

A preferred application of the inventive transmission sensor 1 is depicted in FIG. 5. FIG. 5 shows an oil system 70, e.g., a hydraulic system or a lubricant oil system having essentially any type of equipment 71, which requires oil. The oil circulated in the oil system 70 flows through a loop 72 in which the transmission sensor 1, a switching valve 73 and a water separation device 74, e.g., a coalescer, are arranged. The transmission sensor 1 is arranged in the loop 72 in such a way that the circulated oil flows through the measurement zones 2 and 3. The transmission sensor 1 measures permanently or periodically the impurities accumulating in the oil. Of particular importance here may be the water content in the oil. A corresponding control unit 75 monitors the water content in the oil and communicates with the transmission sensor 1 in this regard. In addition, the control unit 75 is connected to the reversing valve 73. As long as the turbidity detected by the transmission sensor 1 is below a predetermined upper limit, the reversing valve 73 is connected so that the oil in the loop 72 bypasses the water separation device 74 through a bypass 76. Then the oil does not flow through the water separation device 74. However, as soon as the turbidity detected by the transmission sensor 1 has reached the preset upper limit, the control unit 75 reverses the reversing valve 73, so that the oil in the loop 72 again flows through the water separation device 74. In doing so, the water present in the oil, for example, is separated into a container 77. The control unit 75 expediently reverses the switching valve 73 again when a lower limit for the turbidity, i.e., the water content has been reached. Due to this procedure the lifetime of the water separation device 74 is drastically increased, because oil flows through it only when the water content is to be reduced.

In a particular further embodiment, a second transmission sensor 1 may be arranged downstream from the water separation device 74 so that with its help, an optimum operating point of the water separation device 74 can be established. For example, a coalescer may operate optimally only up to a certain volume flow; at a greater volume flow, water may penetrate through the coalescer. This optimum operating point can be established relatively accurately when using a downstream second transmission sensor 1, so that the efficiency of the entire installation is increased.

Instead of the water content in the oil, contamination of oil with solids can also be monitored. For example, the lubricant oil of an internal combustion engine, in particular in a motor vehicle, may be monitored with the help of this transmission sensor 1. Of particular importance here is a form of application in which the transmission sensor 1 in a fluid system, e.g., and oil system, is connected downstream from a filter or an absorber or an adsorber to thereby monitor this separation element for proper functioning. In this way it is possible to detect a decline in separation effect by detecting a corresponding increase in contamination downstream from the separation-element.

The invention claimed is:

1. A transmission sensor suitable for measuring the turbidity of a fluid,
   having a first measurement zone which is or can be filled with a fluid,
   having a second measurement zone which is shorter than the first measurement zone and likewise is or can be filled with fluid,
   having a housing which has a wall that is transparent for electromagnetic radiation at least in the area of the measurement zones,
   having at least one transmitter which is arranged in the housing and emits electromagnetic radiation into the measurement zones through an inlet area in the wall,
   having a first receiver which is arranged in the housing and senses the radiation transmitted through the first measurement zone through a first outlet area in the wall,
   having a second receiver which is arranged in the housing and senses the radiation transmitted through the second measurement zone through a second outlet area in the wall,
   having a transmitter carrier in which the transmitter is placed, where the transmitter necessarily assumes a predetermined aligned position,
   having a receiver carrier into which the receivers are placed, whereby the receivers necessarily assume a predetermined aligned position,
   having a transmitter carrier holder which necessarily positions the transmitter carrier in the housing in a predetermined position at the inlet area,
   having a receiver carrier holder which necessarily positions the receiver carrier in the housing in a predetermined position at the outlet areas;
   wherein the wall has a step in the area of the measurement zones such that wall thickness in the second area is greater than in the first outlet area.

2. The transmission sensor according to claim 1, wherein the transmitter carrier has a first transmitter aperture arrangement assigned to the first measurement zone and a second transmitter aperture arrangement assigned to the second measurement zone between the transmitter and the inlet area.

3. The transmission sensor according to claim 2, wherein at least one of the aperture arrangements is formed by an aperture or by a pair of apertures arranged in alignment or by a tunnel.

4. The transmission sensor according to claim 2, wherein each distance between the transmitter and the receivers is at least approximately ten times longer than an outlet diameter of the transmitter aperture arrangement assigned thereto.

5. The transmission sensor according to claim 1, wherein the receiver carrier has a first receiver aperture arrangement between the first receiver and a first outlet area and has a second receiver aperture arrangement between the second receiver and the second outlet.

6. The transmission sensor according to claim 1, wherein the two receivers are assigned a common transmitter, whereby a linear first beam path extending from the transmitter to the first receiver and a linear second beam path extending from the transmitter to the second receiver intersect in the transmitter.

7. The transmission sensor according to claim 1, wherein the ratio of the length of the second measurement zone to the length of the first measurement zone amounts to a value of at most 5:7 or 5:10.

8. The transmission sensor according to claim 1, wherein a third receiver is provided, this receiver being arranged at the side of the measurement zones in the housing and sensing the radiation scattered in the fluid through a side area in the wall.

9. The transmission sensor according to claim 1, wherein the transmitter is designed so that it can emit different types of electromagnetic radiation which differs in wavelength.

10. Use of a transmission sensor according to claim 1, for detecting solid or liquid impurities in a liquid or a gas.

11. A method of operating a transmission sensor
    having a first measurement zone which is filled by a fluid,
    having a second measurement zone which is shorter than the first measurement zone and is filled with fluid,
    having a housing which has a wall that is transparent for electromagnetic radiation at least in the area of the measurement zones,
    having a transmitter for electromagnetic radiation assigned to the two measurement zones,
    having a first receiver assigned to the first measurement zone sensing the radiation transmitted through the first measurement zone through a first outlet area in the wall, and
    having a second receiver assigned to the second measurement zone sensing the radiation transmitted through the second measurement zone through a second outlet area in the wall,
    wherein the wall has a step in the area of the measurement zones such that wall thickness in the second outlet area is greater than in the first outlet area; and
    wherein a measured calibration is performed in which a first calibration value ($M1_{cal}$) is determined, this value correlating with the intensity of the radiation transmitted through the first measurement zone and in which a second calibration value ($M2_{cal}$) which correlates with the intensity of the radiation transmitted through the second measurement zone is determined and
    to determine a turbidity value which correlates with the turbidity of the fluid
       a first measured value (M1) is determined which correlates with the intensity of the radiation transmitted through the first measurement zone,
       a second measured value (M2) that correlates with the intensity of the radiation transmitted through the second measurement zone is determined,
       a first standardized measured value ($M1_{standard}$) is formed by the quotient first measured value (MI)/first calibration value ($M1_{cal}$),
       a second standardized measured value ($M2_{standard}$) is formed by the quotient second measured value (M2)/second calibration value ($M2_{cal}$),
       the turbidity value is determined from the standardized measured values ($M1_{standard}$) and $M2_{standard}$).

12. The operating method according to claim 11, wherein to determine the turbidity value which correlates with the fluid turbidity, a turbidity factor (f) is determined, this factor being formed by the quotient second standardized measured value ($M2_{standard}$)/first standardized measured value ($M1_{standard}$).

13. The operating method according to claim 11, wherein to determine the turbidity value which correlates with the fluid turbidity, a turbidity factor (f) is determined, this factor being formed by a quotient whose dividend is formed from the difference between the standardized measured values ($M1_{standard}$, $M2_{standard}$) and whose divisor is formed by the sum of the standardized measured values ($M1_{standard}$, $M2_{standard}$).

14. The method according to claim 11, wherein a transmitter calibration is performed in which the transmitter output power of the transmitter is increased incrementally until a predetermined minimum value for the incoming radiation intensity can be detected at both receivers, whereby the transmitter output power which then prevails is used as the operating transmitter output power ($I_{cal}$) at which the transmitter is operated in determination of a turbidity value which correlates with the turbidity of the fluid.

15. The operating method according to claim 14, wherein the incremental increase in the transmitter output power begins at a value of zero in the first step.

16. The operating method according to claim 14, wherein an upper limit value is predetermined for the incremental increase in the transmitter output power, and a suitable error signal is generated when the transmitter output power reaches this upper limit and the predetermined minimum value for the incoming radiation intensity cannot be detected at one of the receivers at least.

17. The operating method according to claim 11, wherein the measured value calibration or the transmitter calibration is performed when the presence of a sufficiently clear fluid is signaled by a higher-level signal.

18. The operating method according to claim 11, wherein a suitable message signal is generated when the turbidity value or the turbidity factor (f) reaches a predetermined threshold value.

19. The operating method according to claim 11, wherein a suitable message signal is generated when the turbidity value or the turbidity factor (f) has reached a predetermined threshold at a predetermined number of directly successive turbidity measurements.

20. The operating method according to claim 11, wherein the curve of the turbidity value or the turbidity factor (f) over time is determined and analyzed.

21. The operating method according to claim 11, wherein the fluid temperature is taken into account in the measured value calibration or in the transmitter calibration or in the determination of the turbidity value or the turbidity factor (f).

* * * * *

UNITED STATES PATENT AND TRADEMARK OFFICE
CERTIFICATE OF CORRECTION

| | | |
|---|---|---|
| PATENT NO. | : 7,060,979 B2 | Page 1 of 1 |
| APPLICATION NO. | : 10/475406 | |
| DATED | : June 13, 2006 | |
| INVENTOR(S) | : Manz et al. | |

It is certified that error appears in the above-identified patent and that said Letters Patent is hereby corrected as shown below:

In Column 11, line 39 (Line 36 of Claim 1) after the word "second", please insert: --outlet--.

In Column 11, line 59 (Line 5 of Claim 5) after the word "outlet" please insert: --area--.

Signed and Sealed this

Twenty-first Day of November, 2006

JON W. DUDAS
*Director of the United States Patent and Trademark Office*